United States Patent
Myers et al.

(10) Patent No.: US 12,257,334 B2
(45) Date of Patent: Mar. 25, 2025

(54) ORAL CARE COMPOSITIONS

(71) Applicant: Colgate-Palmolive Company, New York, NY (US)

(72) Inventors: Carl Myers, Wayne, NJ (US); Rehana Begum-Gafur, Clifton, NJ (US)

(73) Assignee: Colgate-Palmolive Company, New York, NY (US)

( * ) Notice: Subject to any disclaimer, the term of this patent is extended or adjusted under 35 U.S.C. 154(b) by 11 days.

(21) Appl. No.: 17/733,825

(22) Filed: Apr. 29, 2022

(65) Prior Publication Data

US 2022/0331226 A1 Oct. 20, 2022

Related U.S. Application Data

(63) Continuation of application No. 15/366,327, filed on Dec. 1, 2016, now Pat. No. 11,337,912.

(60) Provisional application No. 62/261,791, filed on Dec. 1, 2015.

(51) Int. Cl.
| | | |
|---|---|---|
| *A61K 8/41* | (2006.01) | |
| *A61K 8/39* | (2006.01) | |
| *A61K 8/43* | (2006.01) | |
| *A61K 8/44* | (2006.01) | |
| *A61K 8/46* | (2006.01) | |
| *A61K 8/81* | (2006.01) | |
| *A61K 8/86* | (2006.01) | |
| *A61K 8/90* | (2006.01) | |
| *A61Q 11/00* | (2006.01) | |

(52) U.S. Cl.
CPC ............ *A61K 8/8164* (2013.01); *A61K 8/39* (2013.01); *A61K 8/41* (2013.01); *A61K 8/416* (2013.01); *A61K 8/43* (2013.01); *A61K 8/44* (2013.01); *A61K 8/463* (2013.01); *A61K 8/8147* (2013.01); *A61K 8/86* (2013.01); *A61K 8/90* (2013.01); *A61Q 11/00* (2013.01); *A61K 2800/5422* (2013.01)

(58) Field of Classification Search
None
See application file for complete search history.

(56) References Cited

U.S. PATENT DOCUMENTS

| 5,525,330 A * | 6/1996 | Gaffar ................. A61K 8/4913 424/57 |
|---|---|---|
| 6,479,036 B1 | 11/2002 | Stanier et al. |
| 8,926,997 B1 | 1/2015 | Stockel et al. |
| 2004/0101492 A1* | 5/2004 | Dolan .................... A61K 8/922 424/49 |
| 2006/0140881 A1 | 6/2006 | Xu et al. |
| 2010/0316580 A1 | 12/2010 | Kohli et al. |
| 2011/0052509 A1 | 3/2011 | Subramanyam et al. |
| 2013/0224126 A1* | 8/2013 | Lewus .................. A61Q 11/00 424/54 |
| 2016/0331670 A1 | 11/2016 | Prencipe et al. |

FOREIGN PATENT DOCUMENTS

| RU | 2482835 | 5/2013 | |
|---|---|---|---|
| WO | 2009/099454 | 8/2009 | |
| WO | 2012/064338 | 5/2012 | |
| WO | 2015/094336 | 6/2015 | |
| WO | WO-2015094336 A1 * | 6/2015 | .............. A61K 8/25 |
| WO | 2020/109411 | 6/2020 | |

OTHER PUBLICATIONS

International Search Report and Written Opinion of the International Searching Authority in International Application No. PCT/US2016/064349, mailed Feb. 27, 2017.

* cited by examiner

*Primary Examiner* — Brian Gulledge

(57) ABSTRACT

This application provides, among other things, novel aqueous oral care compositions useful for combining and delivering poorly compatible ingredients, for example to deliver effective levels of cationic antibacterial agents in combination with anionic polymers that protect against erosion and staining, by addition of a stabilizing amount of a polyamine, e.g., lysine, and methods for making and using the same.

13 Claims, No Drawings

ORAL CARE COMPOSITIONS

CROSS-REFERENCE TO RELATED PATENT APPLICATIONS

This application is a continuation of U.S. application Ser. No. 15/366,327, filed on Dec. 1, 2016, which claims the benefit of priority to United States Provisional Patent Application Ser. No. 62/261,791 filed Dec. 1, 2015, the entirety of which is incorporated herein by reference.

BACKGROUND

This application relates, inter alia, to novel aqueous oral care compositions useful for combining and delivering poorly compatible ingredients, for example to deliver effective levels of cationic antibacterial agents in combination with polymers that protect against erosion and staining.

Biofilms form when bacteria adhere to surfaces in some form of watery environment and begin to excrete a slimy, glue-like substance that can stick to all kinds of materials—metals, plastics, soil particles, medical implant materials, biological tissues. Dental plaque is a biofilm that adheres to tooth and other oral surfaces, particularly at the gingival margin, and is implicated in the occurrence of gingivitis, periodontitis, caries and other forms of periodontal disease. Dental plaque is cohesive and highly resistant to removal from teeth and/or oral surfaces. Bacteria associated with dental plaque convert sugar to glucans, which are insoluble polysaccharides that provide plaque with its cohesive properties. Anaerobic bacteria in plaque metabolize sugar to produce acids which dissolve tooth minerals, damaging the enamel and eventually forming dental caries. Saliva can buffer acids produced by bacteria and promote remineralization of the enamel, but extensive plaque can block the saliva from contact with the enamel. Redeposition of minerals in the biofilm forms a hard deposit on the tooth called calculus (or tartar), which becomes a local irritant for the gums, causing gingivitis.

Various antibacterial agents can retard the growth of bacteria and thus reduce the formation of biofilm on oral surfaces. In many cases, these antibacterial agents are cationic, for example quaternary ammonium surfactants such as cetyl pyridinium chloride (CPC), bisguanides such as chlorhexidine, metal cations such as zinc or stannous ions, and guanidines such as arginine.

Everyday activities such as smoking or other oral use of tobacco products, and eating, chewing or drinking certain foods and beverages (particularly coffee, tea, cola drinks, and red wine), cause undesirable staining of surfaces of teeth. Staining can also result from microbial activity, including that associated with dental plaque. The chromogens or color causing substances in these materials become part of the pellicle layer and can permeate the enamel layer. Even with regular brushing and flossing, years of chromogen accumulation can impart noticeable tooth discoloration.

A tooth is comprised of an inner dentin layer and an outer hard enamel layer that is the protective layer of the tooth. The enamel layer of a tooth is naturally opaque, and white or a slightly off-white color. The enamel layer is composed of hydroxyapatite mineral crystals that create a somewhat porous surface. These hydroxyapatite crystals form microscopic hexagonal rods or prisms that make up the enamel surface. As a result, the surface of the enamel presents microscopic spaces or pores between the prisms. Without limiting the mechanism, function, or utility of the present disclosure, it is believed that this porous nature of the enamel is where discoloring substances permeate the enamel and discolor the teeth.

As the compounds that stain the teeth are typically anionic materials, cationic antibacterial agents can cause or enhance staining by facilitating the deposit of chromogens or by forming salts with minerals.

One approach to reducing staining and erosion as well as reducing biofilm formation is the use of anionic polymers that help coat and protect the enamel, discouraging bacterial attachment and repelling chromagens. These polymers, however, can interact with cationic antimicrobial agents, leading to formulation incompatibilities, particularly in high water formulations, such as mouthwashes, and inhibiting delivery of the antimicrobial agent and/or the polymer. Oral care products comprising such polymers are disclosed, for example, in WO 2015094336 A1, incorporated herein by reference.

There is thus a need for novel oral compositions and methods that may inhibit staining and/or biofilm formation.

BRIEF SUMMARY

It is surprisingly found that addition of a stabilizing amount of an orally acceptable polyamine compound, e.g., lysine, to formulations comprising an anionic polymer and a cationic antibacterial agent inhibits the association of these components and enhances delivery to the teeth.

In certain embodiments, the formulations can form an unusual, aqueous biphasic system, where the cationic agent is concentrated in one phase. When the phases are mixed, for example by shaking before use, the cationic agent is delivered in microdroplets having a very high concentration of the active, thus providing improved delivery and a high local concentration of the active at the site of delivery, compared to a homogenous solution of the cationic agent. These formulations differ from conventional biphasic formulations in that both phases are aqueous, rather than one phase being hydrophobic and the other hydrophilic. They also differ from structured compositions such as gels insofar as they separate into phases having different compositions and densities, e.g., an upper phase and a lower phase, which can be readily mixed by shaking and which will then re-separate over a short period.

For example, cetyl pyridinium chloride (CPC) is generally incompatible with anionic polymers because of the resulting precipitation of both components. The addition of lysine provides needed stability and competition between the acid functional groups of the polymer, the acid and the amine functional groups of lysine, and the CPC—the result is to free CPC and make it more available for interaction with bacteria. In some embodiments, the addition of glutamic acid further improves CPC availability through additional competition pathways through the carboxylates on glutamic acid. Without lysine (and optionally glutamic acid), a formulation with CPC and anionic polymers may have little better efficacy than a non-CPC containing material, or the media control.

Similarly, chlorhexidine will generally complex with anionic polymers no matter what steps are taken, given their high charge density and entropically driven precipitation reaction. But we have found that chlorhixidine and anionic polymers can be formulated in such a way to prevent precipitation (or to re-dissolve the precipitate) through the inclusion of lysine (Lys), polyethylene glycol (PEG), and low levels of anionic surfactant, such as sodium lauryl sulfate (SLS). Additional non-ionic surfactant, e.g., poloxamer, can be used to supplement portions of SLS.

The disclosure thus provides, in one embodiment, oral care compositions comprising
(i) an orally acceptable acidic polymer, for example a polymer having an isoelectric point of less than pH 5, e.g., for example selected from one or more of (a) synthetic anionic linear polycarboxylates, such as 1:4 to 4:1 copolymers of maleic anhydride or acid with another polymerizable ethylenically unsaturated monomer, e.g., co-polymers of methyl vinyl ether/maleic anhydride, wherein some or all of the anhydride moieties are hydrolyzed to provide free carboxyl groups, and (b) phosphate/acrylate co-polymers, for example a polymer made up of acrylate monomers and phosphate-bearing monomers, e.g., a co-polymerized product of a mixture of acrylic acid, methacrylic acid, and 2-hydroxyethyl methacrylate phosphates of Formula 1:

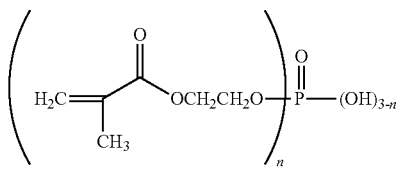

wherein n is 0, 1 or 2; and mixtures thereof; e.g., wherein the orally acceptable acidic polymer has a molecular weight of at least 7500D, e.g., 10 kD to 1500 kD;
(ii) an orally acceptable nonionic polymer, for example selected from one or more poly(alkylene oxide) polymers, e.g., selected from polyethylene glycols, polypropylene glycols, poloxamers and mixtures thereof; e.g., wherein the orally acceptable nonionic polymer has a molecular weight of at least 3000D, e.g., 6 kD to 250 kD;
(iii) an effective amount of orally acceptable cationic active agent, in free or orally acceptable salt form, e.g., selected from one or more of quaternary ammonium surfactants (such as cetyl pyridinium chloride (CPC)), bisguanides (such as chlorhexidine digluconate), cationic amino acids (such as arginine), metal cations (such as zinc, calcium, or stannous ions), or combinations thereof;
(iv) a stabilizing amount of a polyamine, e.g., having an isoelectric point of greater than pH 8.5, e.g., lysine, e.g., which may be added in free or salt form; and
(v) water.

The disclosure further provides methods of inhibiting dental erosion, staining, and/or biofilm formation comprising administering to the oral cavity a composition as described.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As is usual in the art, the compositions described herein are sometimes described in terms of their ingredients, notwithstanding that the ingredients may disassociate, associate or react in the formulation. Ions, for example, are commonly provided to a formulation in the form of a salt, which may dissolve and disassociate in aqueous solution. It is understood that the invention encompasses both the mixture of described ingredients and the product thus obtained.

In a first embodiment, the disclosure provides oral care compositions (Composition 1) comprising
(i) an orally acceptable acidic polymer;
(ii) an orally acceptable nonionic polymer;
(iii) an effective amount of orally acceptable cationic active agent, in free or orally acceptable salt form;
(iv) a stabilizing amount of lysine or polylysine, in free or orally acceptable salt form; and
(v) water.

For example, the disclosure provides embodiments of Composition 1 as follows:
1.1 Composition 1 wherein the orally acceptable acidic polymer is in linear or branched form or mixtures thereof, having acidic functional groups to provide an isoelectric point of pH 5 or less, and optionally additionally having uncharged spacers or side chains, for example comprising hydrophobic moieties (such as methyl methacrylate monomers or alkane chains), and/or uncharged hydrophilic moieties (such as polyalkylene glycols).
1.2 Composition 1 wherein the orally acceptable acidic polymer is selected from one or more of synthetic anionic linear polycarboxylates, phosphate/acrylate co-polymers, and combinations thereof.
1.3 Composition 1 or 1.1 wherein the orally acceptable acidic polymer is selected from one or more of (a) 1:4 to 4:1 copolymers of maleic anhydride or acid with another polymerizable ethylenically unsaturated monomer, e.g., co-polymers of methyl vinyl ether/maleic anhydride, wherein some or all of the anhydride moieties are hydrolyzed to provide free carboxyl groups, and (b) co-polymerized products of a mixture of acrylic acid, methacrylic acid, and 2-hydroxyethyl methacrylate phosphates of Formula 1:

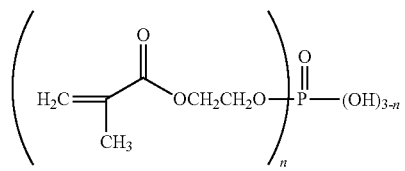

wherein n is 0, 1 or 2; and mixtures thereof;
e.g., wherein the orally acceptable acidic polymer has a molecular weight of at least 7500D, e.g., 10 kD to 1500 kD.

1.4 Any foregoing composition wherein the orally acceptable acidic polymer comprises a phosphate/acrylate co-polymer which is a co-polymerized product of a mixture of acrylic acid, methacrylic acid, and 2-hydroxyethyl methacrylate phosphates of Formula 1:

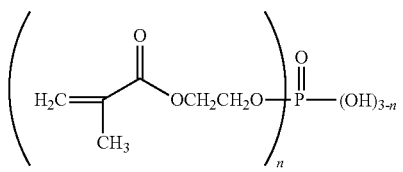

wherein n is 0, 1 or 2.

1.5 Any foregoing composition wherein the orally acceptable acidic polymer comprises a phosphate/acrylate co-polymer, wherein the phosphate/acrylate co-polymer is a co-polymerized product of a mixture of acrylic acid, methacrylic acid, and 2-hydroxyethyl methacrylate phosphates of Formula 1 comprising acrylic acid in a molar percentage of 80-90%, e.g., about 85%; methacrylic acid in a molar percentage of 5-15%, e.g., about 11%, and hydroxyethyl methacrylate phosphates of Formula 1 in a molar percentage of 2-6%, e.g., about 4%.

1.6 Any foregoing composition wherein the orally acceptable acidic polymer comprises a phosphate/acrylate co-polymer, wherein the phosphate/acrylate co-polymer has an average molecular weight of from 10 to 40 kDa, e.g., 20 to 30 kDa.

1.7 Any foregoing composition wherein the orally acceptable acidic polymer comprises a phosphate/acrylate co-polymer, wherein the phosphate/acrylate copolymer is a random copolymer having a weight average molecular weight of about 20,000 to 30,000 grams per mole that is the copolymerized product of a mixture of acrylic acid, methacrylic acid, and 2-hydroxyethy methacrylate phosphates of Formula 1, e.g., in a molar ratio of about 85:11:4.

1.8 Any foregoing composition wherein the orally acceptable acidic polymer comprises 0.1 to 10 weight % phosphate/acrylate co-polymer, e.g., 0.2 to 9 weight % phosphate/acrylate co-polymer, e.g., 0.3 to 8 weight % phosphate/acrylate co-polymer, e.g., 0.4 to 7 weight % phosphate/acrylate co-polymer, e.g., 0.5 to 6 phosphate/acrylate co-polymer, e.g., e.g., 0.5 to 5 weight % phosphate/acrylate co-polymer, e.g., 0.5 to 4 weight % phosphate/acrylate co-polymer, e.g., 0.5 to 3 weight % phosphate/acrylate co-polymer, e.g., 0.5 to 2 weight % phosphate/acrylate co-polymer, e.g., 1 to 10 weight % phosphate/acrylate co-polymer, e.g., 1 to 8 weight % phosphate/acrylate co-polymer, e.g., 1 to 6 weight % phosphate/acrylate co-polymer, e.g., 1 to 5 weight % phosphate/acrylate co-polymer, e.g., 1 to 4 weight % phosphate/acrylate co-polymer, e.g., 1 to 3 weight % phosphate/acrylate co-polymer, e.g., 1 to 2 weight % phosphate/acrylate co-polymer.

1.9 Any foregoing composition wherein the orally acceptable acidic polymer comprises 0.01 to 30 weight % synthetic anionic linear polycarboxylate, e.g., 0.1 to 30 weight % synthetic anionic linear polycarboxylate, e.g., 1 to 30 weight % synthetic anionic linear polycarboxylate, e.g., 5 to 30 weight % synthetic anionic linear polycarboxylate, e.g., 10 to 30 weight % synthetic anionic linear polycarboxylate, e.g., 10 to 20 weight % synthetic anionic linear polycarboxylate, e.g., 15 weight % synthetic anionic linear polycarboxylate, e.g., 17 weight % synthetic anionic linear polycarboxylate.

1.10 Any foregoing composition wherein the orally acceptable acidic polymer comprises a copolymer of maleic anhydride and methyl vinyl ether.

1.11 Any foregoing composition wherein the orally acceptable acidic polymer comprises a 1:4 to 4:1 copolymer of methyl vinyl ether/maleic anhydride (optionally fully or partially hydrolyzed following)-polymerization to provide the corresponding acid).

1.12 Any foregoing composition wherein the orally acceptable acidic polymer comprises a 1:4 to 4:1 copolymer of methyl vinyl ether/maleic anhydride (optionally fully or partially hydrolyzed following co-polymerization to provide the corresponding acid) having a molecular weight (M.W.) of about 30,000 to about 1,000,000, e.g. about 300,000 to about 800,000.

1.13 Any foregoing composition wherein the orally acceptable acidic polymer comprises a combination of a copolymer of maleic anhydride and methyl vinyl ether and phosphate/acrylate co-polymer.

1.14 Any foregoing composition wherein the orally acceptable acidic polymer comprises a combination of (i) a copolymer of maleic anhydride and methyl vinyl ether and (ii) a phosphate/acrylate co-polymer, in a weight ratio of approximately 1:1.

1.15 Any foregoing composition wherein the orally acceptable acidic polymer comprises 0.5% to 2% of a copolymer of maleic anhydride and methyl vinyl ether and 0.5% to 2% of a phosphate/acrylate co-polymer.

1.16 Any foregoing composition wherein the orally acceptable acidic polymer comprises a combination of (i) a 1:4 to 4:1 copolymer of methyl vinyl ether/maleic anhydride (optionally fully or partially hydrolyzed following co-polymerization to provide the corresponding acid) having a molecular weight (M.W.) of about 30,000 to about 1,000,000, e.g. about 300,000 to about 800,000; and (ii) a phosphate/acrylate co-polymer, wherein the phosphate/acrylate co-polymer is a co-polymerized product of a mixture of acrylic acid, methacrylic acid, and 2-hydroxyethyl methacrylate phosphates of Formula 1 comprising acrylic acid in a molar percentage of 80-90%, e.g., about 85%; methacrylic acid in a molar percentage of 5-15%, e.g., about 11%, and hydroxyethyl methacrylate phosphates of Formula 1 in a molar percentage of 2-6%, e.g., about 4%.

1.17 Any foregoing composition wherein the orally acceptable acidic polymer is present in a total amount of 1% to 3%.

1.18 Any foregoing composition wherein the orally acceptable nonionic polymer is selected from one or more poly(alkylene oxide) polymers.

1.19 Any foregoing composition wherein the orally acceptable nonionic polymer is selected from polyethylene glycols, polypropylene glycols, poloxamers, copolymers of polyethylene glycol and polypropylene glycol, and mixtures thereof.

1.20 Any foregoing composition wherein the orally acceptable nonionic polymer has a molecular weight of at least 3000D, e.g., 6 kD to 250 kD.

1.21 Any foregoing compositions wherein the orally acceptable nonionic polymer is selected from polyethylene glycol of MW 5 kDa-35 kDa, poloxamer 407, and mixtures thereof.

1.22 Any foregoing composition wherein the orally acceptable cationic active agent is selected from one or more of quaternary ammonium surfactants (such as cetyl pyridinium chloride (CPC), bisguanides (such as chlorhexidine digluconate), cationic amino acids (such as arginine), metal cations (such as zinc, calcium, or stannous ions), or combinations thereof.

1.23 Any foregoing composition wherein the orally acceptable cationic active agent comprises a pyridinium surfactant, e.g., cetyl pyridinium chloride (CPC).

1.24 Any foregoing composition wherein the orally acceptable cationic active agent comprises chlorhexidine.

1.25 Any foregoing composition wherein the orally acceptable cationic active agent comprises arginine.

1.26 Any foregoing composition wherein the orally acceptable cationic active agent comprises zinc ions.

1.27 Any foregoing composition wherein the orally acceptable cationic active agent is provided by an orally acceptable salt selected from zinc salts, stannous salts, pyridinium salts, and bisguanide salts.

1.28 Any foregoing composition wherein the orally acceptable cationic active agent is provided by an orally acceptable salt selected from cetyl pyridinium chloride and chlorhexidine digluconate.

1.29 Any foregoing composition wherein the orally acceptable cationic active agent is provided by an orally acceptable zinc salt, stannous salt or combination thereof.

1.30 Any foregoing composition wherein the effective amount of cationic active agent, in free or salt form, is present and comprises cetyl pyridinium chloride, in an amount of 0.05 to 0.1%, e.g., about 0.075%.

1.31 Any foregoing composition wherein the effective amount of cationic active agent, in free or salt form, is present and comprises chlorhexidine digluconate, in an amount of 0.1 to 0.2%, e.g., about 0.12%.

1.32 Any foregoing composition wherein the polyamine, in free or orally acceptable salt form, comprises lysine, in free or orally acceptable salt form.

1.33 Any foregoing composition wherein the stabilizing amount of polyamine compound, is an amount sufficient to substantially interfere with interaction between a cationic active agent and the acidic polymer, e.g. an amount sufficient to inhibit formation of a precipitate or reduction of the efficacy of the cationic active agent.

1.34 Any foregoing composition wherein the polyamine is lysine in free or salt form and the composition further comprises glutamic acid, in free or salt form, wherein the combined amount of lysine and glutamic acid is 1 to 10%; e.g., a combination of lysine and glutamic acid in a weight ratio of lysine:glutamic acid of 3:1 to 5:1, wherein the weight % is calculated on the basis of the weight of the free amino acids.

1.35 Any foregoing composition wherein the composition comprises 1%-5% lysine, in free or orally acceptable salt form.

1.36 Any foregoing composition wherein the composition comprises lysine in the form of the hydrochloride salt.

1.37 Any foregoing co reposition wherein the com position comprises 2%-4% lysine hydrochloride.

1.38 Any foregoing composition wherein the compositioncomprises greater than 50% water.

1.39 Any foregoing composition wherein the composition comprises 70% to 95% water.

1.40 Any foregoing composition wherein the composition comprises one or more of a thickener, a buffer, a humectant, a surfactant, an abrasive, a sweetener, a flavorant, a pigment, a dye, an anti-caries agent, an anti-bacterial anent, a whitening agent, a desensitizing agent, a preservative, or a mixture thereof.

1.41 Any foregoing composition wherein the composition comprises a phosphate buffer.

1.42 Any foregoing composition wherein the composition comprises a buffer wherein the buffer comprises sodium hydroxide.

1.43 Any foregoing composition wherein the composition comprises a humectant.

1.44 Any foregoing composition wherein the composition comprises a humectant, wherein the humectant is a mixture of glycerin, sorbitol, and propylene glycol.

1.45 Any foregoing composition wherein the composition comprises an anionic surfactant.

1.46 Any foregoing composition wherein the composition comprises an anionic surfactant, wherein the anionic surfactant comprises sodium lauryl sulfate.

1.47 Any foregoing composition wherein the composition comprises an abrasive.

1.48 Any foregoing composition wherein the composition comprises an abrasive, wherein the abrasive comprises silica.

1.49 Any foregoing composition wherein the composition a sweetener.

1.50 Any foregoing composition wherein the composition a sweetener, wherein the sweetener is sodium saccharin.

1.51 Any foregoing composition wherein the composition comprises a flavorant.

1.52 Any foregoing composition wherein the composition comprises a dye.

1.53 Any foregoing composition wherein the composition comprises an anti-caries agent.

1.54 Any foregoing composition wherein the composition comprises a fluoride ion source.

1.55 Any foregoing composition wherein the composition comprises a fluoride ion source, wherein the fluoride ion source is stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, or a mixture thereof.

1.56 Any foregoing composition wherein the composition comprises a whitening agent.

1.57 Any foregoing composition wherein the composition comprises a whitening agent, wherein the whitening agent is hydrogen peroxide.

1.58 Any foregoing composition wherein the composition comprises a desensitizing agent, a vitamin, a preservative, an enzyme, or a mixture thereof.

1.59 Any foregoing composition wherein the composition is a mouthwash, toothpaste, tooth gel, tooth powder, non-abrasive gel, mousse, foam, mouth spray, lozenge, oral tablet, dental implement, or pet care product.

1.60 Any foregoing composition wherein the composition is a mouthwash.

1.61 Any foregoing composition which is biphasic, e.g., wherein the solution comprises two distinct aqueous phases having different composition and density.

1.62 Any foregoing composition which is biphasic, wherein one phase comprises at least 90% of the orally acceptable acidic polymer, the orally acceptable cationic active agent, and the lysine or polylysine, and the other phase comprises at least 90% of the orally acceptable nonionic polymer.

1.63 Any foregoing composition which comprises less than 5%, e.g., less than 2% of hydrophobic ingredients.

1.64 Any foregoing composition which is essentially oil-free, apart from flavoring agents.

1.65 Any foregoing composition having a pH of 5.5 to 8.0.

1.66 Any foregoing composition having a pH of 5.5 to 6.5.

1.67 Any foregoing composition further comprising an anionic surfactant.

1.68 Any foregoing composition further comprising sodium lauryl sulfate, e.g., 0.1-1.5%.

1.69 Any foregoing composition wherein
  (i) the orally acceptable acidic polymer comprises a mixture of (a) a copolymer of maleic anhydride and methyl vinyl ether in an amount of 0.5 to 1.5% and (b) a phosphate/acrylate co-polymer, in an amount of 0.5 to 1.5%;
  (ii) the orally acceptable nonionic polymer comprises polyethylene glycol having a molecular weight of 5 kD to 20 kD in an amount of 0 to 3% and poloxamer 407 in an amount of 0 to 1%, in a combined amount of 1 to 3%;
  (iii) an effective amount of orally acceptable cationic active agent, in free or orally acceptable salt form, comprises chlorhexidine, in an amount of 0.1 to 0.2%
  (iv) the lysine or polylysine, in free or orally acceptable salt form, is lysine in free or orally acceptable salt form, in an amount of 0.5 to 3%; and
  (v) the amount of water is 70-95%;
  wherein the composition optionally further comprises sodium lauryl sulfate in an amount of 0-1%, e.g., 0.1-1%;
  wherein all amounts are by weight of the total composition.

Further claimed is the use of lysine or polylysine, in free or orally acceptable salt form, to stabilize an oral care formulation comprising an orally acceptable acidic polymer, an orally acceptable nonionic polymer, and an effective amount of orally acceptable cationic active agent, in free or orally acceptable salt form; for example use in any of the foregoing Compositions 1, et seq.

As used herein, an "oral care composition" refers to a composition for which the intended use can include oral care, oral hygiene, or oral appearance, or for which the intended method of use can comprise administration to the oral cavity. The term "oral care composition" thus specifically excludes compositions which are highly toxic, unpalatable, or otherwise unsuitable for administration to the oral cavity. In some embodiments, an oral care composition is not intentionally swallowed, but is rather retained in the oral cavity for a time sufficient to affect the intended utility. The oral care compositions as disclosed herein may be used in nonhuman mammals such as companion animals (e.g., dogs and cats), as well as by humans. In some embodiments, the oral care compositions as disclosed herein are used by humans. Oral care compositions include, for example, dentifrice and mouthwash. In some embodiments, the disclosure provides mouthwash formulations.

As used herein, "orally acceptable" refers to a material that is safe and palatable at the relevant concentrations for use in an oral care formulation, such as a mouthwash or dentifrice.

As used herein, "orally acceptable carrier" refers to any vehicle useful in formulating the oral care compositions disclosed herein. The orally acceptable carrier is not harmful to a mammal in amounts disclosed herein when retained in the mouth, without swallowing, for a period sufficient to permit effective contact with a dental surface as required herein. In general, the orally acceptable carrier is not harmful even if unintentionally swallowed. Suitable orally acceptable carriers include, for example, one or more of the following: water, a thickener, a buffer, a humectant, a surfactant, an abrasive, a sweetener, a flavorant, a pigment, a dye, an anti-caries agent, an anti-bacterial, a whitening agent, a desensitizing agent, a vitamin, a preservative, an enzyme, and mixtures thereof.

As used herein, "orally acceptable cationic active agent" means an agent which is cationic in aqueous solution at neutral pH and which provides some benefit, e.g. antimicrobial, antigingivitis, and/or antierosion activity, to the teeth or oral cavity. While in aqueous formulation, the agent will generally be in solution, but it may be introduced to the formulation formulated in free or orally acceptable salt form. In certain embodiments, the orally acceptable cationic active agent is selected from one or more of quaternary ammonium surfactants (such as cetyl pyridinium chloride (CPC)), bis-guanides (such as chlorhexidine digluconate), cationic amino acids (such as arginine), metal cations (such as zinc, calcium, or stannous ions), or combinations thereof.

As used herein, "orally acceptable acidic polymer" means an orally acceptable polymer comprising monomers bearing acidic groups, for example carboxy and/or phosphate groups, for example selected from one or more of synthetic anionic linear polycarboxylates and phosphate/acrylate co-polymers. The acidic polymer should have a relatively low isoelectric point, e.g., pH 5 or less. The appropriate molecular weight will vary depending on the specific polymer, the degree of crosslinking or branching, and the proportion of acidic functional groups, but in general, the molecular weight is greater than 5000 g/mol. In various embodiments, the acidic polymer could be in a linear or nonlinear (i.e. branched) form or a mixture of linear and branched forms, the backbone or side chains could contain various hydrophobic moieties such as methyl methacrylate monomers, alkane chains, etc., and/or as hydrophilic uncharged moieties such as PEG or PPG, as well as moieties bearing acidic functional groups. Examples of acidic polymers include synthetic anionic linear polycarboxylates, phosphate/acrylate co-polymers, and combinations thereof. can be selected from a variety of anionic polymers backbones including vinyl, acrylic, maleic. Carboxylate moieties along the polymer backbone can come from the monomers themselves, such as in the case of acrylic acid, methacrylic acid, or maleic acid, or can be generated from the hydrolysis of the polymer, such as in the case of poly-butyl acrylate. The acidic polymer can be made up of copolymers or homopolymers of acidic functional monomers or mixtures thereof.

As used herein, an "orally acceptable nonionic polymer" is a water soluble polymer which does not form an ionic species at relevant pH, e.g., between pH 3 and 10, for example in certain embodiments selected from one or more poly(alkylene oxide) polymers, e.g., selected from polyethylene glycols (PEG), polypropylene glycols (PPG), poloxamers (block co-polymers of PEG and PPG), random copolymers of PEG and PPG, and mixtures thereof. In some embodiments, the orally acceptable nonionic polymer has a molecular weight of at least 3000D, e.g., 6 kDa to 250 kDa. The molecular weight may vary depending on the particular type of polymer, the degree of branching, if any, and the concentration used. Experiments with PEG having molecular weight between 6 kDa and 35 kDa, for example, showed that at lower concentrations, e.g., for a 3% concentration in a particular combination with other ingredients, a higher molecular weight material, e.g. 35 kDa, was needed to form the biphasic system, but at formulations having higher levels of PEG, a PEG having a lower molecular weight, e.g., 6 kDa could support a biphasic system. In particular embodiments, the nonionic polymer comprises a mixture of (i) polyethylene glycol (MW 5 kDa-35 kDa) and (ii) poloxamer (i.e., an ethylene oxide/propylene oxide block copolymer), e.g., poloxamer 407, which is a triblock copolymer consisting of a central hydrophobic block of polypropylene glycol flanked by two hydrophilic blocks of polyethylene glycol, wherein the approximate length of the two PEG blocks is about 101 repeat units while the approximate length of the propylene glycol block is about 56 repeat units, available commercially for example as Pluronic F127 (BASF).

As used herein "polyamine compound" means a molecule having at least two primary or secondary amine groups, for example having an isoelectric point of greater than pH 8.5, for example pH 9-10. Examples of polyamines include ethylene diamine, lysine, or histadine, as well as polymers such as Lupasol P, which is a polyethylenimine. The polymine must be safe for its intended use. Where the composition is an oral care composition, the polymaine must be orally acceptable. The polyamine may be provided in free or acid addition salt form. In certain embodiments the polyamine compound is lysine.

As used herein, "biphasic" refers to stable liquid compositions which contain at least two distinct homogeneous phases, having different densities, such that the phases are separate at rest. The phases may be readily mixed by shaking but will then re-separate over a short period, e.g., less than half an hour. In certain embodiments, the term excludes gels, emulsions, microemulsions, and homogeneous solutions. In certain embodiments, these formulations differ from conventional biphasic formulations in that both phases are aqueous, rather than one phase being hydrophobic and the other hydrophilic.

As used herein, "isoelectric point" is the pH in aqueous solution where the molecule has no net charge. The isoelectric point of lysine, for example, occurs at pH 9.7 due to its two amines and one carboxylic acid (at this point only one amine is positive and the acid is negative). At every other pH, Lys contains some degree of charge whether overall positive (<pH 9.7, both amines are protonated) or negative (>pH 9.7, both amines are deprotated—neutral—and the acid group has a negative charge). The acidic polymer, e.g., either DV8801 or Gantrez S-97, will only have an isoelectric point at low pH <5 at the point where the carboxylates are all protonated resulting in a net 0 charge. The stabilized system exists between the isoelectric points of the necessary materials.

As used herein, "phosphate/acrylate co-polymer" refers to a polymer made up of acrylate monomers and phosphate-bearing monomers, e.g., a co-polymerized product of a mixture of acrylic acid, methacrylic acid, and 2-hydroxyethyl methacrylate phosphates of Formula 1:

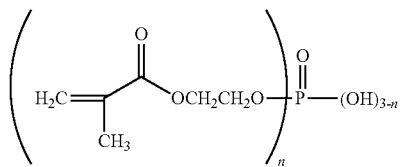

wherein n is 0, 1 or 2. In some embodiments, the phosphate/acrylate co-polymer is a co-polymerized product of a mixture of acrylic acid, methacrylic acid, and 2-hydroxyethyl methacrylate phosphates of Formula 1, comprising acrylic acid in a molar percentage of 80-90%, e.g., about 85%; methacrylic acid in a molar percentage of 5-15%, e.g., about 11%, and hydroxyethyl methacrylate phosphates of Formula I. in a molar percentage of 2-6%, e.g., about 4%. In some embodiments, the phosphate/acrylate co-polymer has an average molecular weight of from 10 to 40 kDa, e.g., 20 to 30 kDa. Phosphate/acrylate co-polymers as described include commercially available polymers, e.g. DV8801 (Rhodia). The phosphate side group of a phosphate/acrylate co-polymer, as disclosed herein, may function as an anchor to deposit the co-polymer onto the tooth surface thereby forming a physical layer on the tooth surface that may inhibit staining and/or biofilm formation. For example, in a particular embodiment (the embodiment used in the Examples below the phosphate/acrylate copolymer is a random copolymer having a weight average molecular weight of about 20,000 to 30,000 grams per mole that is the copolymerized product of a mixture of, in the relative amounts set forth in Table 1 below, 2-hydroxyethy methacrylate phosphates, acrylic acid, and iriethacrylic; acid.

TABLE 1

| Monomer Name and Structure | Monomer Weight Ratio (weight %) | Monomer Molar Ratio (Mole %) |
|---|---|---|
| 2-hydroxyethyl methacylate phosphates $\left(H_2C=\underset{CH_3}{C}-\overset{O}{\underset{\|}{C}}-OCH_2CH_2O\right)_n\overset{O}{\underset{\|}{P}}-(OH)_{3-n}$ mixture of n = 0, n = 1, and n = 2 | 11 | 4 |
| acrylic acid $H_2C=\underset{H}{C}-\overset{O}{\underset{\|}{C}}-OH$ | 75 | 85 |

TABLE 1-continued

| Monomer Name and Structure | Monomer Weight Ratio (weight %) | Monomer Molar Ratio (Mole %) |
|---|---|---|
| methacrylic acid 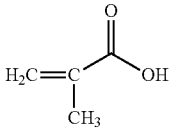 | 14 | 11 |

As used herein, "synthetic anionic linear polycarboxylate" refers to a polymer synthesized by using an olefinically or ethylenically unsaturated carboxylic acid that contains an activated carbon-to-carbon olefinic double bond and at least one carboxyl group. The acid contains an olefinic double bond that readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrilacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other olefinic monomers copolymerizable with such carboxylic monomers include vinyl acetate, vinyl chloride, dimethyl maleate and the like. The synthetic anionic linear polycarboxylate is mainly a hydrocarbon with optional halogen and 0-containing substituents and linkages as present in for example ester, ether, and OH groups. The copolymers preferably contain sufficient carboxylic salt groups for water-solubility. The terms "synthetic" and "linear" do not include known thickening or gelling agents comprising carboxymethylcellulose and other derivatives of cellulose and natural gums, nor Carbopols having reduced solubility due to cross-linkages.

In some embodiments, "synthetic anionic linear polycarboxylate" refers to 1:4 to 4:1 copolymers of maleic anhydride or acid with another polymerizable ethylenically unsaturated monomer, e.g., methyl vinyl ether (methoxyethylene), having a molecular weight (M.W.) of about 30,000 to about 2,500,000; for example 1:4 to 4:1, e.g. about 1:1, copolymers of methyl vinyl ether/maleic anhydride, wherein the anhydride is hydrolyzed following co-polymerization to provide the corresponding acid, having a molecular weight (M.W.) of about 30,000 to about 1,000,000, e.g. about 300,000 to about 800,000, e.g., as sold under the trade name GANTREZ®, e.g., GANTREZ® S-97 Pharmaceutical Grade (M.W. ca. 700,000), available from Ashland Specialty Chemicals, Bound Brook, N.J. 08805.

As used herein, a "tartar control agent" refers to a compound or a mixture of compounds that inhibit the formation of tartar, a mixture of calcium phosphates on organic matrices, and/or the deposition of plaque on teeth to form tartar (calculus).

As used herein, "chemical stain" refers to a discoloration of a dental surface caused by adsorption or absorption of a colored agent on or into the surface, or caused by chemical reaction of material of the dental surface (e.g., dental enamel) with a colored or noncolored agent contacting the surface. "Chemical staining" herein means formation and/or development of a chemical stain.

As used herein, "dental surface" refers to a surface of a natural tooth or a hard surface of artificial dentition including a crown, cap, filling, bridge, dental implant and the like. In some embodiments, the dental surface is a natural tooth.

The compositions are, for example, oral care compositions, in accordance with Composition 1, et seq. for example mouthwashes. Any of the compositions of Composition 1, et seq. is suitable for oral care use, provided the ingredients are orally acceptable. In some embodiments, the mouthwash of Composition 1 comprises an effective amount of an orally acceptable cationic active agent, which is an antimicrobial, antigingivitis, anti-erosion and/or anti-caries agent, e.g. a cationic active agent selected from one or more of quaternary ammonium surfactants (such as cetyl pyridinium chloride (CPC)), bisguanides (such as chlorhexidine digluconate), cationic amino acids (such as arginine), metal cations (such as zinc, calcium, or stannous ions), or combinations thereof. The orally acceptable cationic active agent may be present in an effective amount, for example an antimicrobial, antigingivitis, anti-erosion and/or anti-caries amount. The precise amount will depend on the particular active agent and the condition to be treated or prevented, but in various embodiments, antimicrobially effective levels of CPC in a mouthwash would include amounts from 0.05 to 0.1%, e.g., about 0.075%; antimicrobially effective levels of chlorhexidine digluconate in a mouthwash would include amounts from 0.1-0.2%, e.g., about 0.12%; anti-erosion or antimicrobial levels of metal cations such as zinc (e.g., zinc citrate or other soluble salt) or stannous (e.g., stannous fluoride and/or stannous chloride) would be on the order of 100-1500 ppm.

The oral care composition used in the present disclosure comprise significant levels of water. Water employed in the preparation of commercial oral compositions should be deionized and free of organic impurities. The amount of water in the compositions includes the free water that is added plus that amount which is introduced with other materials.

Mouthwashes frequently contain significant levels of ethanol, which is often needed to solubilize essential oils and to prevent bacterial contamination. High levels of ethanol may be undesirable, because in addition to the potential for abuse by ingestion, the ethanol may exacerbate conditions like xerostoma. Accordingly, in some embodiments, the oral care compositions of the invention are substantially free of ethanol, e.g., contain less than 1% ethanol.

Humectants can enhance the viscosity, mouthfeel, and sweetness of the product, and may also help preserve the product from degradation or microbial contamination. Suitable humectants include edible polyhydric alcohols such as glycerin, sorbitol, xylitol, propylene glycol as well as other polyols and mixtures of these humectants. Sorbitol may in some cases be provided as a hydrogenated starch hydrolysate in syrup form, which comprises primarily sorbitol (the product if the starch were completely hydrolyzed to glucose, then hydrogenated), but due to incomplete hydrolysis and/or presence of saccharides other than glucose, may also include other sugar alcohols such mannitol, maltitol, and longer chain hydrogenated saccharides, and these other sugar alcohols also function as humectants in this case. In some embodiments, humectants are present at levels of 5% to 30%, e.g., 10% to 20% by weight.

Flavorings for use in the present invention may include extracts or oils from flavorful plants such as peppermint, spearmint, cinnamon, wintergreen, and combinations thereof, cooling agents such as menthol, methyl salicylate, and commercially available products such as OptaCool® from Symrise, as well as sweeteners, which may include polyols (which also function as humectants), saccharin, acesulfame, aspartame, neotame, stevia and sucralose.

Further provided is a method (Method A) for the treatment and/or inhibition of a chemical stain, plaque, and/or tartar on a dental surface, comprising contacting the dental surface with any of the preceding oral care compositions.

Further provided herein is Method A as follows:
A.1 Method A wherein the composition is Composition 1, e.g., 1.1-1.69.
A.2 Method A or A.1 wherein the method is for the treatment of a chemical stain, plaque, and/or tartar on the dental surface.
A.3 Method A.2 wherein the method is for the treatment of a chemical stain on the dental surface.
A.4 Method A.2 wherein the method is for the treatment of plaque on the dental surface.
A.5 Method A.2 wherein the method is for the treatment of tartar on the dental surface.
A.6 Method A or A.1 wherein the method is for the inhibition of a chemical stain, plaque, and/or tartar on the dental surface.
A.7 Method A.6 wherein the method is for the inhibition of a chemical stain on the dental surface.
A.8 Method A.6 wherein the method is for the inhibition of plaque on the dental surface.
A.9 Method A.6 wherein the method is for the inhibition of tartar on the dental surface.
A.10 Method A or A.1-A.9 wherein the dental surface is a human tooth.
A.11 Method A or A.1-A.10 wherein the composition is contacted with the dental surface by brushing.
A.12 Any foregoing Method A, et seq. wherein the formulation is biphasic and is shaken before use.

Further provided is a method (Method B) for the treatment and/or inhibition of gum disease comprising contacting the oral cavity with any of the preceding oral care compositions.

Further provided herein is Method B as follows:
B.1 Method B wherein the composition is Composition 1, e.g., 1.1-1.69.
B.2 Method B or B.1 wherein the method is for the treatment of gum disease.
B.3 Method B, B.1, or B.2 wherein the gum disease is gingivitis.
B.4 Method B, B.1, or B wherein the gum disease is periodontitis.
B.5 Method B or B.1 wherein the method is for the inhibition of gum disease.
B.6 Method B, B.1, or B.5 wherein the gum disease is gingivitis.
B.7 Method B, B.1, or B.5 wherein the gum disease is periodontitis.
B.8 Method B or B.1-B.7 wherein the oral cavity is a human oral cavity.
B.9 Method B or B.1-B.8 wherein the composition is contacted with the oral cavity by brushing.
B.10 Any foregoing Method B, et seq. wherein the formulation is biphasic and is shaken before use.

Further provided is a method (Method C) for the treatment and/or inhibition of ha itosis comprising contacting the oral cavity with any of the preceding oral care compositions.

Further provided herein is Method C as follows:
C.1 Method C wherein the composition is Composition 1, e.g., 1.1-1.69.
C.2 Method C or C.1 wherein the oral cavity is a human oral cavity.
C.3 Method C, C.1, or C.2 wherein the composition is contacted with the oral cavity by brushing.
C.4 Any foregoing Method C, et seq. wherein the formulation is biphasic and is shaken before use.

Further provided is a method (Method D) for inhibiting biofilm formation on a dental surface comprising contacting the dental surface with any of the preceding oral care compositions.

Further provided herein is Method D as follows:
D.1 Method D wherein the composition is Composition 1, e.g., 1.1-1.69.
D.2 Method D or D.1 wherein the dental surface is a human tooth.
D.3 Method D, D.1, or D.2 wherein the composition is contacted with the dental surface by brushing.
D.4 Any foregoing Method) et seq. wherein the formulation is biphasic and is shaken before use.

Further provided is a method (Method E) for treating and/or inhibiting bacteria from sticking together and growing into bigger colonies in an oral cavity comprising contacting the oral cavity with any of the preceding oral care compositions.

Further provided herein is Method E as follows:
E.1 Method E wherein the composition is Composition 1, e.g., 1.1-1.69.
E.2 Method E or E.1 wherein the oral cavity is a human oral cavity.
E.3 Method E, E.1, or E.2 wherein the composition is contacted with the oral cavity by brushing.
E.4 Any foregoing Method E, et seq. wherein the formulations biphasic and is shaken before use.

Further provided are Compositions 1, et seq. for use in any of Methods A-E.

As used herein, "inhibition" refers to reduction of stains that would otherwise form or develop subsequent to the time of the treatment. Such inhibition can range from a small but observable or measurable reduction to complete inhibition of subsequent staining, by comparison with an untreated or placebo-treated dental surface.

Where the dental surface is substantially free of chemical stains, Method A, e.g., A.1-A.12, is effective to inhibit formation and development of new chemical stains, as can occur for example by oral use of tobacco products (including smoking) or by drinking tea, coffee, red wine, or coke, subsequent to treatment according to the method. Where the dental surface already possesses some degree of chemical staining, Method A, e.g., A.1-A.12, is effective to inhibit further development of the existing stain. In some embodiments, the Method A, e.g., A.1-A.12, can remove, partially or completely, an existing chemical stain as well as inhibit subsequent staining.

EXAMPLES

Example 1

Chlorhexidine and Anti-Stain Polymers

Chlorhexidine (CHX) mouthwash is very effective to fight gingivitis. But after CHX has been adsorbed to a tooth surface, stains often result after drinking coffee, tea, or red wine, primarily occurring through charge interaction between the positively charged CHX and negatively charged stains. This means that someone using a chlorhexidine must either avoid foods and beverages with a dark color, or become accustomed to teeth that are more yellow and stained.

Rhodia DV8801 (also sometimes called Mirapol 8801 or DV) is a phosphate/acrylate co-polymer from Solvay, which exhibits significant stain fighting ability, and when used in oral care products, deposits onto a tooth surface. However, when DV and CHX are combined, complexes formed by the two can result in precipitation of both CHX and DV, inactivating both components.

We have found, however, that CHX and DV can be formulated in such a way to prevent precipitation (or to re-dissolve the precipitate) through the inclusion of lysine (Lys), polyethylene glycol (PEG), and low levels of sodium lauryl sulfate. Additionally, the non-ionic surfactant Poloxamer 407 can be used to supplement portions of SLS. A variety of formulations having ranges as follows are tested:

TABLE 2

Test formulations

| Materials | Range (wt. %) |
| --- | --- |
| Chlorhexidine digluconate | 0.12–0.2 |
| DV8801 (phosphate/acrylate co-polymer) | 0.02–1.0 |
| Gantrez S-97 (copolymer of methyl vinyl ether/maleic anhydride) | 0.02–1 |
| Lysine hydrochloride | 0.25–1 |
| Sodium lauryl sulfate (anionic surfactant) | 0–1 |
| Poloxamer 407 (non-ionic surfactant) | 0–1 |
| PEG 10K (non-ionic surfactant) | 0–3 |
| Water | q.s. |

Stain reduction: The efficacy of the test formulations on staining is tested against a commercial 0.12% chlorhexidine digluconate (CHX) mouthwash. FIG. 1 compares the change in color (W) of hydroxyapatite (HAP) discs treated with various solutions. Each HAP disc is incubated in purified saliva for 3 hours. After this time, the discs are rinsed with water and then transferred to the solutions listed for 15 minutes. They are then rinsed and transferred back into saliva for minutes. This process is repeated three times, after which they are subjected to staining in red wine for 15 minutes, and the change in color (AW) is measured.

The results are as follows:

TABLE 3

Stain protection with various formulations

| Compositions (wt. %) | Commercial 0.12% CHX | 1 DV/ 1 S-97/ 1 Lys | 0.12 CHX/ 1 DV/ 1 S-97/ 1 Lys/ 0.8 SLS | 0.12 CHX/ 1 DV/1 S-97/ 1 Lys/ 0.8 SLS/ 2 PEG 10K |
| --- | --- | --- | --- | --- |
| ΔW | 33.2 | 13.4 | 16.3 | 4.1 |

CHX = chlorhexidine digluconate; DV = DV8801 (phosphate/acrylate co-polymer); S-97 = Gantrez S-97 (copolymer of methyl vinyl ether and maleic anhydride); Lys = lysine hydrochloride; SLS = sodium lauryl sulfate (anionic surfactant); PEG 10K = polyethylene glycol having molecular weight ca. 10 kD (non-ionic surfactant).

As expected, the discs treated with commercial chlorhexidine mouthwash and red wine exhibit considerable staining. A solution of 1% DV8801, 1% Gantrez S-97 and 1% lysine (second column) contains no chlorhexidine and contains anti-stain polymers (DV8801 and Gantrez S-97), so as expected staining is reduced. A solution of 0.12% chlorhexidine digluconate, 1% DV8801, 1% Gantrez S-97, 1% lysine, and 0.8% sodium lauryl sulfate (SLS) exhibits only slightly greater staining than the formulation with the anti-stain polymers alone, showing that the anti-staining polymers in combination with the lysine can still protect against staining precipitated by chlorhexidine. Finally, the addition of 2% of polyethylene glycol to this formulation resulted in very good stain protection, even better than seen with the anti-stain polymers alone.

Deposition of chlorhexidine on HAP: The next question is whether the chlorhexidine in combination with the anti-staining polymers is still adequately deposited for bacterial efficacy. HAP discs are exposed to solutions 1-6 as listed in Table 4, and then extracted with ethanol to determine the level of chlorhexidine that adsorbed to the surface.

TABLE 4

CHX deposition

| Solution | Composition (wt %) | Deposited HAP (ppm) |
| --- | --- | --- |
| 1 | H$_2$O only | 0 |
| 2 | 0.12 CHX | 21.5 +/− 1.3 |
| 3 | 0.12% CHX commercial mouthwash | 12.7 +/− 2.0 |
| 4 | 0.12 CHX/1 DV/1 S-97/1 Lys | 0 |
| 5 | 0.12 CHX/1 DV/1 S-97/1 Lys/0.8 SLS | 26.6 +/− 1.5 |
| 6 | 0.12 CHX/1 DV/1 S-97/1 Lys/0.8 SLS/ 2 PEG 10K | 16.0 +/− 1.7 |

In the presence of either 0.12% chlorhexidine digluconate or commercial mouthwash containing 0.12% chlorhexidine digluconate (solutions 2 and 3), antibacterially effective levels of chlorhexidine are deposited. When chlorhexidine digluconate is combined with the acidic polymers (DV and Gantrez S-97), and Lys alone (solution 4), no CHX is deposited on to the HAP surface, likely because existed as a precipitate and is unable to interact sufficiently with the HAP surface. The addition of SLS in samples 5 and 6 brings CHX back into solution, and re-enables its ability to deposit to HAP. Formulation 6 has deposition efficacy comparable to a commercial formulation, but also exhibits superior anti-staining properties, surprisingly showing that it is possible to maximize both the deposition of the chlorhexidine and the anti-staining efficacy of the acidic polymers.

Bacterial kill: A 20-second short interval kill test (SIKT) measures the efficacy of various treatment solutions in killing oral pathogens. The Fluorescent SIKT uses Live/Dead BacLight fluorescent viability staining system to measure permeabilization of bacteria by single actives or liquid formulations. A mixed species inoculum culture containing: *Lactobacillus casei, Streptococcus oralis, Actinomyces viscosus, Veillonella parvula* & *Fusobacterium nucleatum* at an optical density of 0.5 @ 610nm is centrifuged. The supernatant is then aspirated off and the remaining pellicle re-suspended in sterile phosphate buffered saline (PBS). 100 ul of this solution is then treated with 100 ul of test sample for 30 or 60 seconds. Immediately following treatment, the exposure is neutralized by adding 1.3 ml of sterile D/E neutralizing broth. The neutralizing broth is then rinsed off by centrifugation and re-suspension in PBS. 50 ul samples are then transferred in triplicate to a 96-well microplate. The fluorescent dyes are then prepared per the manufacturer's directions and added to the samples. The fluorescence is then measured in a fluorescent plate reader. Data from this assay are presented as a percentage of bacterial remaining viable relative to a control sample treated with PBS.

TABLE 5

SIKT with different formualtions

| Compositions (wt. %) | Commercial 0.12% CHX | Dead | 0.12 CHX/ 1 DV | 0.12 CHX/ 1 DV/1 S-97/ 1 Lys/0.8 SLS/ 2 PEG 10K |
|---|---|---|---|---|
| % viability | 34.9 | 36.3 | 116.4 | 36.6 |

The sample labeled "dead" represents that sample in which pure ethanol is used as a high-efficiency bacteriocide. In this particular example, the commercial mouthwash containing 0.12% chlorhexidine digluconate exhibits similar effects to that of ethanol. A solution containing 0.12% CHX/1% DV demonstrated no bacteria kill effect, probably due to complexation and precipitation of the active ingredients. As such, no kill effect was expected or observed. Sample #4 shows significant kill effect, and is comparable to commercial mouthwash containing 0.12% chlorhexidine digluconate, suggesting similar high efficacy.

Because SLS contains its own antibacterial effects, we performed a series of control SIKT experiments, listed in Table 6:

TABLE 6

SIKT with different formulations

| Solution # | Composition (wt %) | % Viability |
|---|---|---|
| 1 | Commercial 0.12% CHX | 25.9 |
| 2 | 2 PEG 10k/1 DV/1 S-97/ 0.5 Lys/0.4 SLS/0.5 Poloxamer 407 | 78.1 |
| 3 | 2 PEG 10k/1 DV/1 S-97/ 0.5 Lys/0.4 SLS/0.5 Poloxamer 407/0.12 CHX | 38.4 |
| 4 | 2 PEG 10k/1 DV/1 S-97/ 0.5 Lys/0.4 SLS/0.5 Poloxamer 407/0.2 CHX | 38.8 |
| 5 | 1 Poloxamer 407 | 92.2 |
| 6 | 0.2 SLS | 31.0 |
| 7 | PBS | 100 |
| 8 | Dead (Ethanol) | 28.4 |

As compared to the control solution 7, the commercial 0.12% CHX mouthwash provided a significant decrease in viability, to 25.9%. Solution 6, containing only SLS also provides a significant decrease in viability, to 31%. Solution 2 represents the full formulation in the absence of CHX to determine the effect of SLS on bacteria. In the absence of CHX, a viability of 78.1% is observed. Adding 0.12 or 0.2% CHX, as in solutions 3 and 4, returns the overall solution efficacy to 38.4 and 38.8% viability, respectively. This suggests that in the presence of the full formulation, the effect of SLS is masked by the other materials. But that base formulation is nevertheless able to deliver affective levels of CHX.

Stabilization with Multi-Charged Species: The addition of DV to a solution of CHX causes an immediate precipitation. However, the addition of low levels of surfactants or multi-charged compounds brings both DV and CHX back into solution. The table below lists multiple compounds that help to redissolve the DV-CHX, and what we have found as their lowest effective levels. These solutions are stable from pH 4.9-7. Addition of citric acid to lower the pH to <4.9 causes significant precipitation.

TABLE 7

Materials added to a solution containing 0.12 or 0.2 CHX (w/w by actives) and 1.025 DV (w/w by actives)

| Material | Lowest effective level |
|---|---|
| Betaine | 0.3% for 0.12% CHX 0.3% for 0.2% CHX (With significant stirring time) |

Example 2

Exemplary Mouthwash Formulation with Chlorhexidine and Anti-Stain Polymers

A mouthwash formulation is prepared as follows:

TABLE 8

Formulation with 2.5 DV/0.12 CHX/0.5 SLS; pH adjusted to 6 using citric acid

| Material | Level | % Active | 270 g Batch Use Level |
|---|---|---|---|
| Betaine | 0.0000% | 30.00% | 0.000 |
| DV8801 | 2.5000% | 41.00% | 16.463 |
| CHX (20%) | 0.1200% | 20.00% | 1.620 |
| Glycerin | 7.2000% | 100.00% | 19.440 |
| Sorbitol | 9.6000% | 100.00% | 25.920 |
| Citric Acid | 0.0004% | 100.00% | 0.001 |
| Propylene Glycol | 7.0000% | 100.00% | 18.900 |
| Peppermint Oil | 0.1000% | 100.00% | 0.270 |
| H2O | 0.0000% | | 181.99 |
| Total | | | 270.000 |

The invention claimed is:

1. An oral care composition comprising:
   a) an orally acceptable acidic polymer wherein said orally acceptable acidic polymer comprises 1:4 to 4:1 copolymers of maleic anhydride or acid with another polymerizable ethylenically unsaturated monomer, wherein some or all of the anhydride moieties are hydrolyzed to provide free carboxyl groups;
   b) an orally acceptable nonionic polymer;
   c) an effective amount of orally acceptable cationic active agent, in free or orally acceptable salt form;
   d) a stabilizing amount of a polyamine compound, in free or orally acceptable salt form;
   e) water; and
   f) an anionic surfactant;
   wherein the composition is a mouthwash which is a biphasic solution comprising two distinct aqueous phases having different composition and density.

2. The composition of claim 1 wherein the orally acceptable nonionic polymer is selected from polyethylene glycols, polypropylene glycols, poloxamers and mixtures thereof.

3. The composition of claim 1 wherein the orally acceptable cationic active agent is selected from one or more of quaternary ammonium surfactants, bisguanides, cationic amino acids, metal cations, and combinations thereof.

4. The composition of claim 1 wherein the orally acceptable cationic active agent is provided by an orally acceptable salt selected from zinc salts, stannous salts, chlorhexidine digluconate, and cetyl pyridinium chloride.

5. The composition of claim 1 wherein the orally acceptable cationic active agent is chlorhexidine digluconate, at a concentration of 0.1%-0.2%.

6. The composition of claim 1 wherein the polyamine, in free or orally acceptable salt form, is lysine hydrochloride.

7. The composition of claim 1 wherein the composition comprises 70% to 95% water.

8. The composition of claim 1 wherein the composition comprises one or more of a thickener, a buffer, a humectant, a surfactant, an abrasive, a sweetener, a flavorant, a pigment, a dye, an anti-caries agent, an anti-bacterial agent, a whitening agent, a desensitizing agent, a preservative, or a mixture thereof.

9. The composition of claim 1 which comprises less than 5% of hydrophobic ingredients.

10. The composition of claim 1 which is essentially oil-free, apart from flavoring agents.

11. The composition of claim 1 having a pH of 5.5 to 8.0.

12. The composition of claim 1 wherein there is no discernable precipitation or reaction between the orally acceptable acidic polymer and the orally acceptable cationic active agent after three months of storage at room temperature.

13. The composition of claim 1 wherein
a) the orally acceptable acidic polymer comprises a mixture of (a) a copolymer of maleic anhydride and methyl vinyl ether in an amount of 0.5 to 1.5% and (b) a phosphate/acrylate co-polymer, in an amount of 0.5 to 1.5%;
b) the orally acceptable nonionic polymer comprises polyethylene glycol having a molecular weight of 5kD to 20kD in an amount of 0 to 3% and poloxamer 407 in an amount of 0 to 1%, in a combined amount of 1 to 3%;
c) the effective amount of orally acceptable cationic active agent, in free or orally acceptable salt form, comprises chlorhexidine, in an amount of 0.1 to 0.2%;
d) the polyamine compound, in free or orally acceptable salt form, is lysine in free or orally acceptable salt form, in an amount of 0.5 to 3%; and
e) the water is present in an amount of 70-95%;
wherein the composition optionally further comprises sodium lauryl sulfate in an amount of up to 1%; and
wherein all amounts are by weight of the total composition.

* * * * *